United States Patent
Renfrew et al.

[11] Patent Number: 6,136,172
[45] Date of Patent: Oct. 24, 2000

[54] GEL-FORMING INSERT FOR ELECTROPHORESIS GELS

[75] Inventors: John A. Renfrew, Burlington; Eric Steinbach; Stuart MacMillan, both of Toronto, all of Canada

[73] Assignee: Visible Genetics Inc., Toronto, Canada

[21] Appl. No.: 09/470,024

[22] Filed: Dec. 22, 1999

Related U.S. Application Data

[63] Continuation of application No. 08/885,531, Jun. 30, 1997.

[51] Int. Cl.[7] .................................................. G01N 27/26
[52] U.S. Cl. ......................... 204/456; 204/620; 249/205; 264/219; 264/279; 264/271.1
[58] Field of Search ................................ 264/271.1, 279, 264/259, 219, 299, 275; 249/105, 205; 204/456, 620, 619

[56] References Cited

U.S. PATENT DOCUMENTS

| | | | |
|---|---|---|---|
| 4,416,761 | 11/1983 | Brown et al. | 204/620 |
| 4,929,329 | 5/1990 | Danby et al. | 204/608 |
| 5,073,246 | 12/1991 | Chu et al. | 204/619 |
| 5,164,066 | 11/1992 | Yetman et al. | 204/619 |
| 5,281,322 | 1/1994 | Antoinette et al. | 204/619 |
| 5,284,565 | 2/1994 | Chu et al. | 204/619 |
| 5,338,426 | 8/1994 | Shigeura et al. | 204/461 |

FOREIGN PATENT DOCUMENTS

| | | |
|---|---|---|
| 0157280 | 10/1985 | European Pat. Off. . |
| 0534135 | 3/1993 | European Pat. Off. . |
| 0555143 | 8/1993 | European Pat. Off. . |
| 2273783 | 6/1994 | United Kingdom . |
| 9219975 | 11/1992 | WIPO . |

*Primary Examiner*—Jill Warden
*Assistant Examiner*—Alex Noguerola
*Attorney, Agent, or Firm*—Oppedahl & Larson LLP

[57] ABSTRACT

Electrophoresis gels are formed using a gel-forming insert having a beveled edge which results in loading sites having a beveled bottom surface. The gel forming insert can have a continuous beveled edge across the entire width of the gel, in which case a special loading insert is used which matches the bevel of the gel. Alternatively, the gel forming insert may be formed with a plurality of fingers with beveled ends, each finger defining a well in the gel. In one form of the gel-forming insert, the fingers are formed from a soft, flexible polymer such as silicone applied on a rigid support.

32 Claims, 4 Drawing Sheets

GEL-FORMING INSERT FOR ELECTROPHORESIS GELS

This application is a continuation of U.S. patent application Ser. No. 08/885,531, filed Jun. 30, 1997.

This application discloses related subject matter to that disclosed in U.S. patent application Ser. No. 08/836,269, filed May 1, 1997, which is now U.S. Pat. No. 5,885,431 and which is the U.S. national phase of PCT/US95/14531 filed Oct. 31, 1995, which is a continuation-in-part of U.S. patent application Ser. No. 08/332,577 filed Nov. 1, 1994, now U.S. Pat. No. 5,627,022, all of which are incorporated herein by reference.

BACKGROUND OF THE INVENTION

This application relates to a gel-forming insert for use in forming electrophoresis microgels of the type which can be used in medical diagnosis, especially for the sequencing of nucleic acids, and to methods of making and using such gels.

International Patent Publication No. WO93/00986 describes electrophoresis gels with a thickness of 25 to 250 microns. The gels are formed between two clamped-together plates, one of which is grooved to a depth equal to the desired gel thickness to form parallel tracks which are then filled with gel. Other formats for very thin electrophoresis gels are described in the parent application, U.S. Pat. No. 5,627,022, and in commonly assigned U.S. Pat. Nos. 5,599,434 and 5,618,398, which are incorporated herein by reference.

In utilizing thin electrophoresis gels, an important challenge is the introduction of a significant number of samples at defined locations along the starting edge of the gel. U.S. Pat. No. 4,929,329 discloses the use of a comb to define a plurality of sample-receiving wells in an electrophoresis gel as is hardens or to cut a plurality of wells into the top surface of an already hardened gel. Formation of sample wells using a comb included during the hardening process requires the subsequent removal of the comb, which can result in damage to the gel structure if not carefully carried out, and this risk increases as the thickness of the gel decreases. Similarly, cutting wells into an already hardened gel may result in a lack of uniformity which will negatively impact on gel performance.

U.S. Pat. No. 5,281,322 discloses an electrophoresis cassette in which so-called "well spacers" are used to define the wells. These spacers are integral extensions of the plates defining the gel arranged in a line along one edge of the plates. Sample wells are formed by filling the area between the plates to such an extent that the gel extends only partially into the space between adjacent spacers. This approach avoids potential damage to the gel due to the insertion or removal of a well-forming comb, but has its own limitations. In particular, the size of the wells is limited to those into which gel-forming solution can be reproducibly introduced, since variations in the depths of the wells or unevenness in the gel surface within a well can result in electrophoresis results which are difficult to interpret.

It would therefore be desirable to provide an apparatus for defining sample introduction locations in an electrophoresis gel which provides very consistent and reproducible well structures and which does not lead to significant instances of gel destruction. It is an object of the present invention to provide such an apparatus.

SUMMARY OF THE INVENTION

These and other objects of the invention are achieved by forming electrophoresis gels using a gel-forming insert having a beveled edge which results in loading sites having a beveled bottom surface. The gel forming insert can have a continuous beveled edge across the entire width of the gel, in which case a special loading insert is used which matches the bevel of the gel. Alternatively, the gel forming insert may be formed with a plurality of fingers with beveled ends, each finger defining a well in the gel. In a particularly preferred gel-forming insert, the fingers are formed from a soft, flexible polymer such as silicone applied on a rigid support.

DETAILED DESCRIPTION OF THE INVENTION

Figure 1:
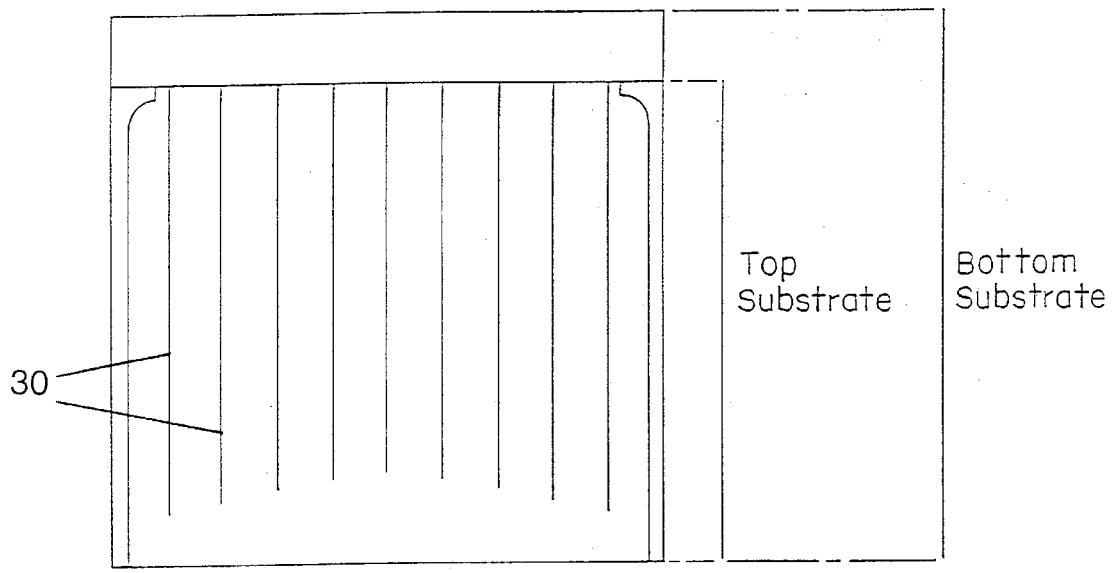
FIG. 1 shows a microgel holder which may be filled using the apparatus of the invention.
Figure 2A:
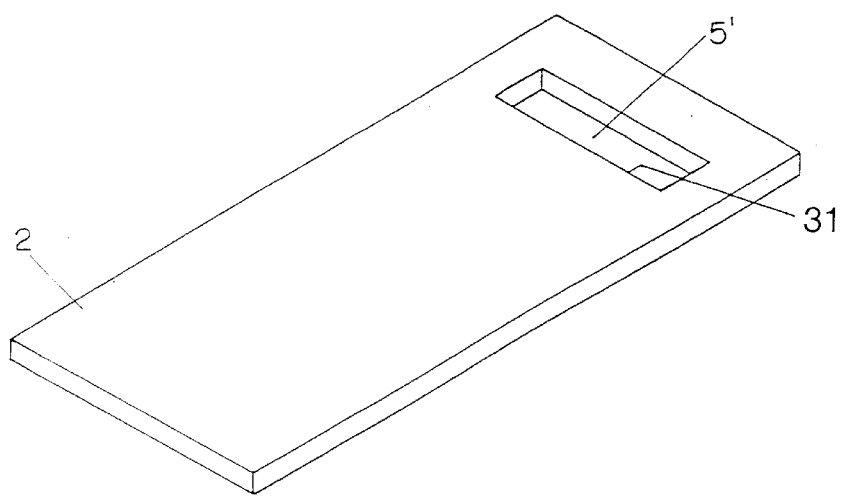
FIGS. 2A and 2B show a further embodiment of a microgel holder which may be filled using the apparatus of the invention.
Figure 2B:
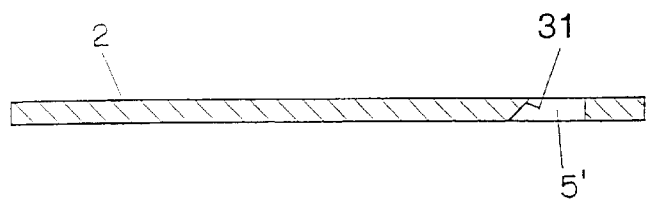

FIGS. 1 and 2A and 2B show microgel formats which can be used with the gel-forming inserts of the invention. In each case, a microgel holder is formed from a bottom substrate and a top substrate, separated by a spacer. The spacer and the interior surfaces of the two substrates define a gel compartment which is to be filled with the electrophoresis gel.

In the microgel holder shown in FIG. 1, spacers have been used to create lane markers 30 within the body of the gel. Such lane markers may be incorporated to separate every lane, every fourth lane, or at such other intervals as may be preferred by the user. The top substrate in this case is shorter than the bottom substrate, and it has been found to be advantageous to extend the lanes beyond the end of the top substrate across at least a part of the extending portion of the bottom substrate. This results in all lanes filling individually from the bottom up, and eliminates the possibility of unpolymerized gel from one lane spilling over into an adjacent lane and causing a bubble to form in the middle of that lane.

FIGS. 2A and 2B show a variation of a top substrate 2 with a window 5' cut therein to permit loading of sample. The edges of the window are all cut at 90°, except for the lower edge which is cut with a 30 to 60°, preferably a 45° bevel, as shown most clearly in FIG. 2B. This design permits improved sample loading.

Figure 3A:
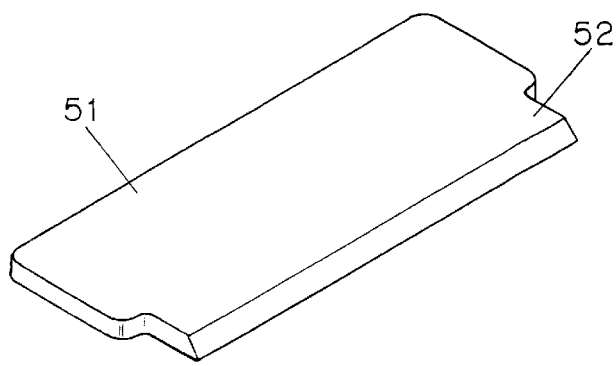
FIGS. 3A and 3B show a gel-forming insert in accordance with the claimed invention.

A microgel using a top substrate cut as shown in FIGS. 2A and 2B is preferably formed using a gel-forming insert in accordance with the invention. A first embodiment of such an insert is shown in FIG. 3A. This insert has a base portion 51 and an insert portion 52. The insert portion 52 is notched at each end, such that it is narrower than the base portion. Preferably, the size of each notch is from 2–4 mm to 5 mm. The free edge of the insert portion is beveled to match the bevel formed in the lower edge 31 of the window 5', and the overall size of the insert is selected to permit insertion of the insert into the window 5'. For example, suitable dimensions are 12.5 cm wide, 1.5 cm in total height and 1 mm in thickness. A tab or handle may be placed on one surface of the base portion 31 to facilitate removal.

Figure 3B:
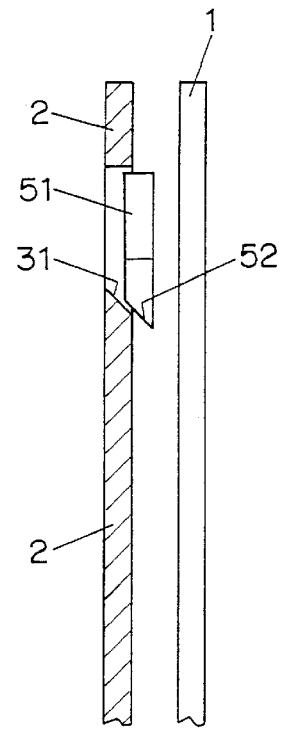

The gel forming insert is placed into the window as shown in FIG. 3B prior to the polymerization of the gel, preferably prior to the filling of the gel compartment. Adhesive tape may be used to constrain the movement of the gel forming insert so as to secure it against the bottom substrate and to prevent its floating on the injected solution. Upon injection of the proper amount of polymerizable solution into the microgel holder, the solution fills up the microgel compartment, up to the gel forming insert, where the solution flows partly around the edges of the gel forming insert, and it may bleed out of the microgel holder through the air holes. If there is a substantial excess of solution injected into the gel holder, the solution may even run out through the top. The excess gel is not of any significant consequence to the effective polymerization, sample loading, or use of the gel, and may be trimmed away if desired.

After UV catalyzed polymerization, it is important to the successful use of a microgel of the invention to delicately remove the gel forming insert without damaging the gel. After polymerization, if the gel holder is tilted into its facial plane, the gel forming insert will tend to fall forward. Gentle tapping on the bottom plate may be necessary to encourage the displacement of the gel forming insert. Once an edge of the gel forming insert has emerged from the plane of the top substrate, it may be grasped and gently pulled away from any polymerized gel which may be in contact with the gel forming insert. Alternatively, adhesive tape attached to the outside face of the gel forming insert may be used to pull the gel forming insert from its position. Either way, care should be taken to preserve the even edge of gel which will have formed along the bottom of the window of the top substrate.

Removal of the gel-forming insert shown in FIG. 3A results in the formation of a trough running across the width of the gel bounded by the beveled edge of the window, the gel itself, and the bottom substrate into which the sample can be inserted. It is into this trough which sample is loaded for electrophoresis.

Figure 4:
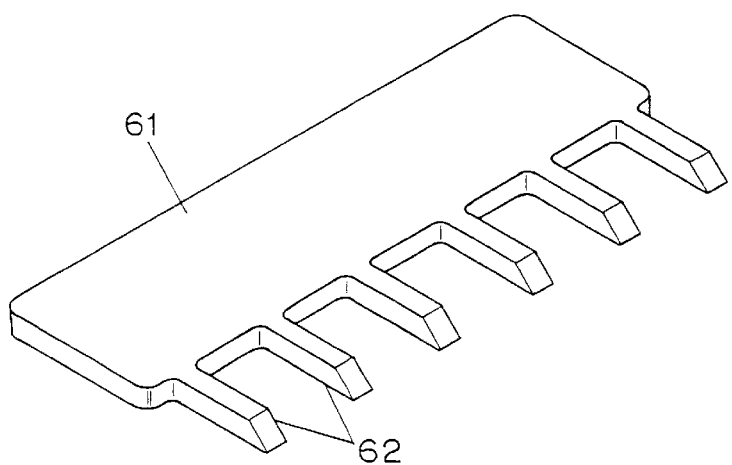
FIG. 4 shows a loading insert useful in combination with the gel-forming insert of FIG. 3A.

Because this trough is continuous across the width of the gel, it lacks the slots normally used in the loading of sample onto a gel. It is therefore desirable to use a specially adapted loading insert of the type shown in FIG. 4 when loading sample onto a gel formed as described above. The insert has a substantially rectangular base portion 61 having two long edges and two short edges; and a plurality of fingers 62 extending from one long edge of the base portion. Each of the fingers preferably has a width of from 0.5 to 3 mm. The fingers are evenly spaced at intervals of 2 to 7 mm in a region along the long edge of the base portion staring and ending at a point from 2 to 4 mm from the adjacent short edge of the base portion so that the fingers fit within the trough. The fingers further have a 30–60° bevel at the distal end thereof to match the bevel of the loading insert and the lower edge of the window. This insert is placed into the trough formed by the gel forming insert, and sample is then loaded into the gaps between the fingers.

A second and alternative method of preparing and loading a microgel, requires forming the microgel in the presence of a gel-forming insert which has a series of flattened bevel-ended fingers which will form wells for the loading of sample on the gel. This gel-forming insert replaces the gel forming insert during the microgel filling and polymerization process. The dimensions of the polymerization comb insert are identical to the gel forming insert, except that instead of having a flat bottom edge beveled to be complementary to the bottom edge of the window in the top substrate, a notch of about 2 mm width and about 5 mm depth is made at intervals, e.g, every 7 mm, along the bottom edge. The result is a row of teeth, each tooth having a bottom edge beveled at to be complementary to the bottom edge of the window in the top substrate. Once placed in the open window of the microgel holder, the gel-forming insert may be sealed in place with adhesive tape such that the entire window is completely covered. An opening for the air holes is then introduced into the adhesive tape. Solution is then injected into the microgel holder. The solution fills the microgel compartment and flows into the gaps in the teeth of the gel-forming insert. Excess solution bleeds out of the air holes. The solution may then be polymerized with UV induced catalysis as described in the invention. When polymerization is complete, the adhesive tape and the polymerization comb insert are gently removed, leaving a row of gel columns vertically disposed against the bottom substrate. The gel columns act to define wells which can be used to separate samples loaded by the conventional methods. Prior to the construction of the microgel holder, the gel compartment faces of the top substrate and bottom substrate may be treated with Bind Silane (Pharmacia).

Figure 5A:
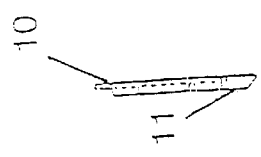
FIGS. 5A and 5B show a plan and cross-sectional view of a further embodiment of a gel-forming insert of the invention.
Figure 5B:
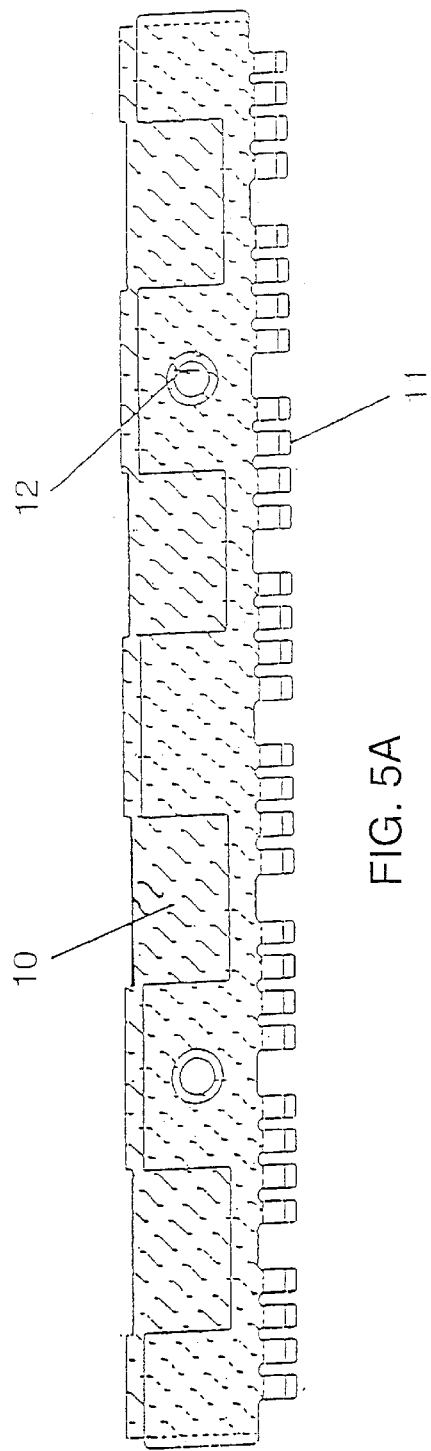
Figure 6A:
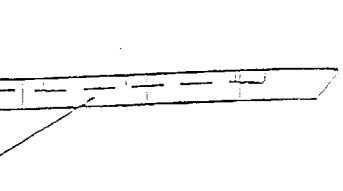
FIG. 6A and 6B show a plan and cross-sectional view of a further embodiment of a gel-forming insert of the invention.
Figure 6B:
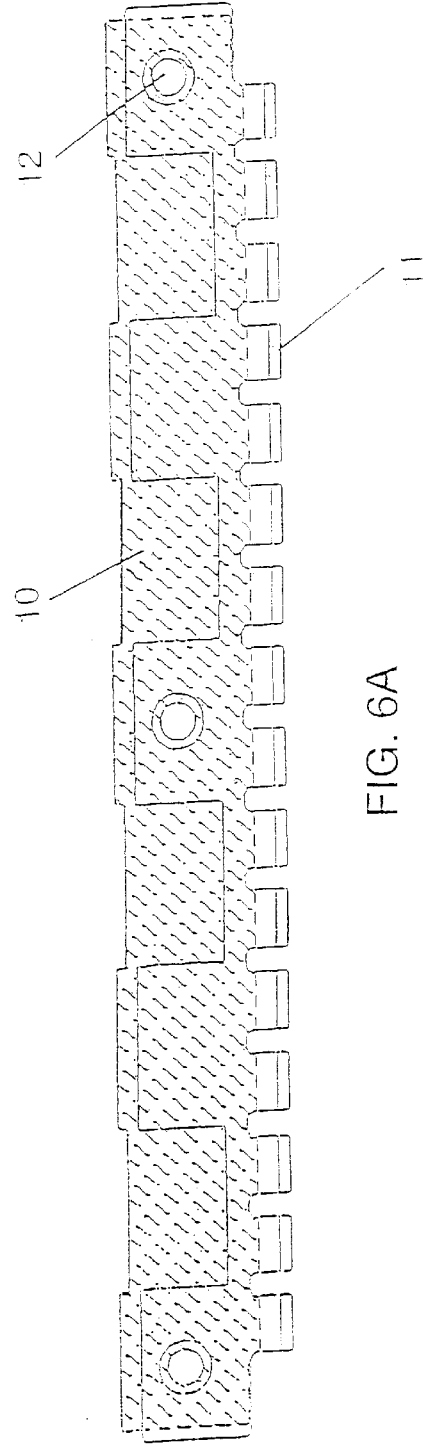

FIGS. 5 and 6 show two versions of a preferred embodiment of the invention. In these embodiments, the gel-forming insert is formed from two pieces, a rigid support member 10 and a flexible edge member 11 which is adhered thereto. The bevel-ended fingers are formed from the flexible material which is easily deformed. This flexibility, combined with the bevel-ended shape makes the gel-forming insert more removed from a hardened gel without damage to the gel.

The support member 10 can be made from any thin, rigid material. A preferred material is 0.015 inch thick sheet stainless steel, although other metals or plastics could be used. The flexible edge member 11 is molded to form the edge member, which can be continuous as in FIG. 3A or separated into fingers as in FIGS. 5 and 6, and adhered to the support member 10. Suitable materials for the flexible edge member include silicone. The fingers are suitably about 1 mm thick, tapering to a thickness of less than 50 $\mu$m for use in forming a gel having a thickness 50 $\mu$m. Thicker or thinner fingers may be employed for thicker or thinner gels.

The gel-forming insert of FIGS. 5 and 6 can be formed by injection or insert molding. Injection molding is a widely used technique in which a mold is created from a solid material and a hardenable material is injected into the mold and hardened, thus creating an inverse replica of the mold. Insert molding is similar except that a solid part is placed into the mold and the hardenable material is injected around it.

For a gel-forming insert according to the invention, insert molding is preferably employed. A mold of the proper dimensions is prepared from a tooled steel or a stainless steel. A stainless steel part is placed inside the mold cavity. Since positioning of the insert is crucial, positioning holes 12 in the steel part are used to align the part on pegs inside the cavity. Liquid silicone is then injected into the cavity. The liquid silicone takes the shape of the cavity and molds itself around the stainless steel part. The silicone is then hardened by a standard method such as heating or chemical catalysis.

The inserted solid part can optionally be made of a hard plastic which is easier and less costly to manufacture.

The preferred hardenable material for the invention is liquid silicone. Other materials besides silicone could be employed, such as plastics, rubber or other materials so long as in their hardened state they are flexible and compliant enough to fill irregularities in the bevel and create a good seal, and are chemically compatible with acrylamide so as not to inhibit polymerization.

Figure 7A:
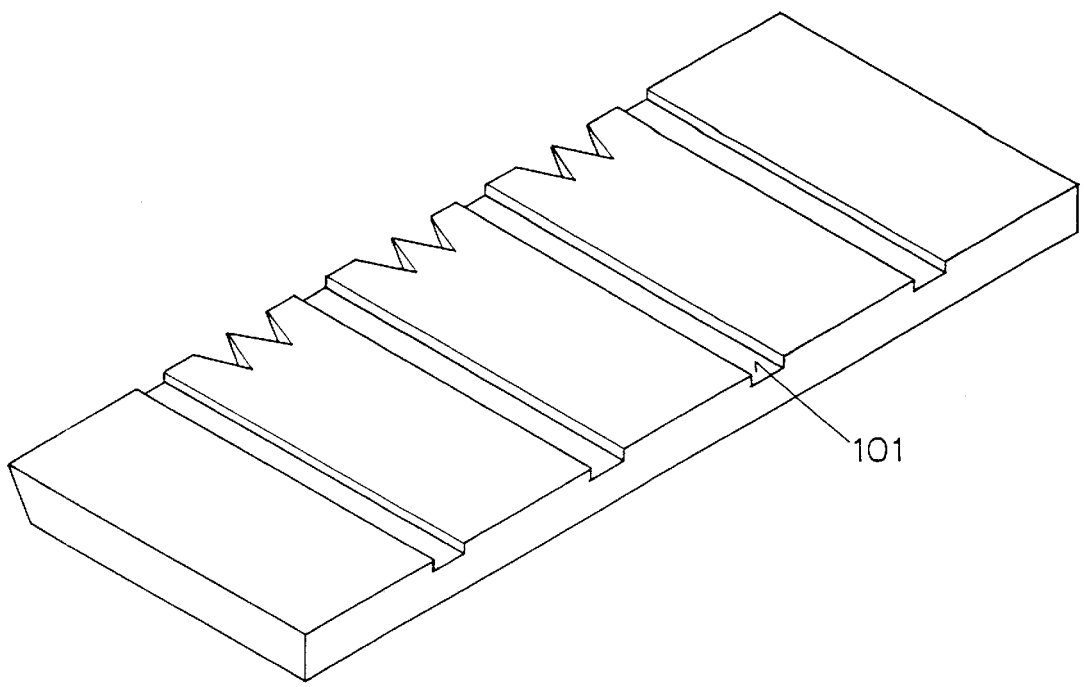
FIGS. 7A and 7B show further embodiments of loading and gel forming inserts in accordance with the invention.
Figure 7B:
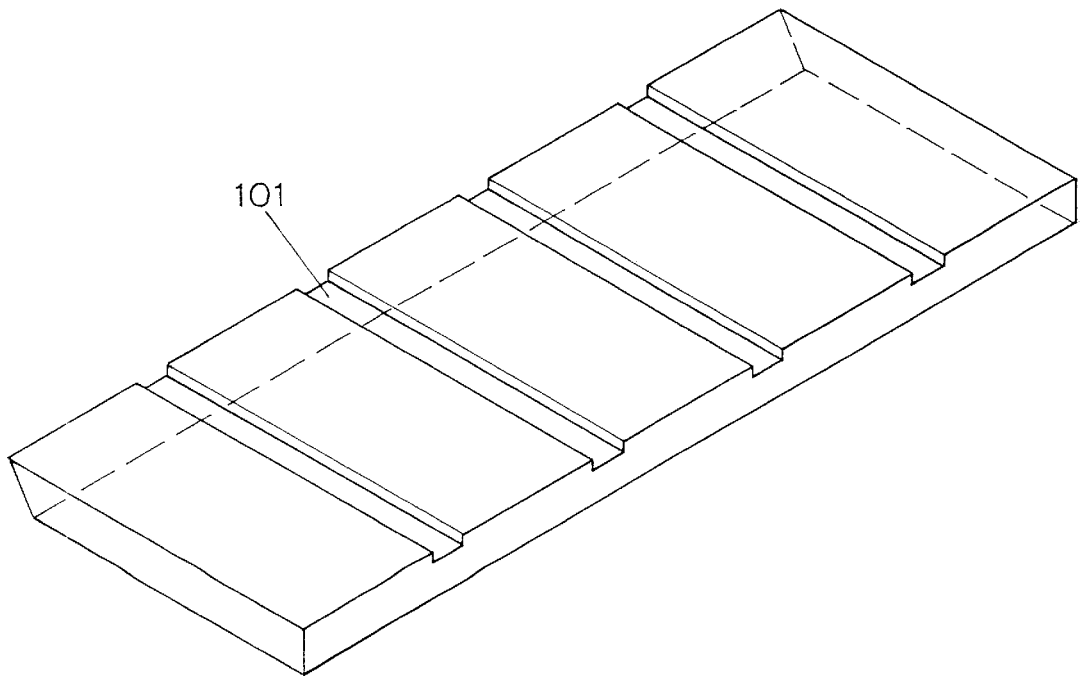

FIGS. 7A and 7B shows alternative designs for gel-forming insert and loading insert useful when the lane dividers are present on the extended portion of the bottom substrate (FIG. 1). In this case, grooves 101 are formed along one surface of the inserts to accommodate the lane dividers. Advantageously, the grooves are slightly wider than the lane dividers to allow for air and excess gel to escape during the filling process.

The gel-forming inserts of the invention provide consistent sample well formation in the end of even very thin microgels and are readily removed without damage to a hardened gel.

What is claimed is:

1. A gel forming insert for use in defining one or more sample-receiving wells in an electrophoresis gel when a gel is polymerized around the insert, wherein the insert comprises a substantially rectangular planar body member having two long edges and two short edges, and upper and lower faces, and said body member comprises a base portion extending along a first of the long edges and an insert portion extending along a second of the long edges, wherein the base portion is formed from a rigid material and the insert portion is formed from an inherently flexible and compliant material, different from the rigid material, wherein the insert portion is in the form of a continuous solid blade effective to form a single sample receiving through or is divided into a plurality of fingers, each pair of fingers having substantially parallel edges which define a gap lying between the fingers in which gel will polymerize when the insert is used to form an electrophoresis gel; and wherein the edge of the insert portion is beveled at an angle of from 30 to 60 degrees such that the lower surface of the body member is larger than the upper surface.

2. The insert of claim 1, wherein the insert portion is divided into a plurality of fingers to define a plurality of sample-receiving wells, and each finger is separated from adjacent fingers by a space into which gel can flow to provide a barrier between adjacent sample-receiving wells.

3. The insert of claim 2, wherein each finger is wider than the space between adjacent fingers.

4. The insert of claim 2, wherein the fingers are formed in groups of four, and the spaces between fingers within a group are smaller than the spaces between adjacent fingers belonging to different groups.

5. The insert of claim 1, wherein the insert portion is formed from silicone.

6. The insert of claim 5, wherein the insert portion is divided into a plurality of fingers to define a plurality of sample-receiving wells, and each finger is separated from adjacent fingers by a space into which gel can flow to provide a barrier between adjacent sample-receiving wells.

7. The insert of claim 6, wherein each finger is wider than the space between adjacent fingers.

8. The insert of claim 6, wherein the fingers are formed in groups of four, and the spaces between fingers within a group are smaller than the spaces between adjacent fingers belonging to different groups.

9. The insert of claim 1, wherein the base portion is formed from metal.

10. The insert of claim 9, wherein the insert portion is formed from silicone.

11. The insert of claim 10, wherein the insert portion is divided into a plurality of fingers to define a plurality of sample-receiving wells, and each finger is separated from adjacent fingers by a space into which gel can flow to provide a barrier between adjacent sample-receiving wells.

12. The insert of claim 11, wherein each finger is wider than the space between adjacent fingers.

13. The insert of claim 11, wherein the fingers are formed in groups of four, and the spaces between fingers within a group are smaller than the spaces between adjacent fingers belonging to different groups.

14. A method for forming an electrophoresis gel having one or more sample-receiving wells formed therein, comprising the steps of inserting a gel-forming insert into a gel holder, introducing gel-forming solution into the gel holder in an amount sufficient to fill the space within the gel holder, polymerizing the gel-forming solution within the gel holder and removing the gel-forming insert to form the electrophoresis gel having one or more sample wells, wherein the gel forming insert defines the one or more sample-receiving wells in electrophoresis gel when a gel is polymerized around the insert, wherein the insert comprises a substantially rectangular planar body member having two long edges and two short edges, and upper and lower faces, and said body member comprises a base portion extending along a first of the long edges and an insert portion extending along a second of the long edges, wherein the base portion is formed from a rigid material and the insert portion is formed from an inherently flexible and compliant material, different from the rigid material, wherein the insert portion is in the form of a continuous solid blade effective to form a single sample receiving through or is divided into a plurality of fingers, each pair of fingers having substantially parallel edges which define a gap lying between the fingers in which gel will polymerize when the insert is used to form an electrophoresis gel; and wherein the edge of the insert portion is beveled at an angle of from 30 to 60 degrees such that the lower surface of the body member is larger than the upper surface.

15. The method of claim 14, wherein the insert portion is divided into a plurality of fingers to define a plurality of sample-receiving wells, and each finger is separated from adjacent fingers by a space into which gel can flow to provide a barrier between adjacent sample-receiving wells.

16. The method of claim 15, wherein each finger is wider than the space between adjacent fingers.

17. The method of claim 15, wherein the fingers are formed in groups of four, and the spaces between fingers within a group are smaller than the spaces between adjacent fingers belonging to different groups.

18. The method of claim 14, wherein the insert portion is formed from silicone.

19. The method of claim 17, wherein the insert portion is divided into a plurality of fingers to define a plurality of sample-receiving wells, and each finger is separated from adjacent fingers by a space into which gel can flow to provide a barrier between adjacent sample-receiving wells.

20. The method of claim 19, wherein each finger is wider than the space between adjacent fingers.

21. The method of claim 19, wherein the fingers are formed in groups of four, and the spaces between fingers within a group are smaller than the spaces between adjacent fingers belonging to different groups.

22. The method of claim 14, wherein the base portion is formed from metal.

23. The method of claim 22, wherein the insert portion is formed from silicone.

24. The method of claim 23, wherein the insert portion is divided into a plurality of fingers to define a plurality of sample-receiving wells, and each finger is separated from adjacent fingers by a space into which gel can flow to provide a barrier between adjacent sample-receiving wells.

25. The method of claim 24, wherein each finger is wider than the space between adjacent fingers.

26. The method of claim 24, wherein the fingers are formed in groups of four, and the spaces between fingers within a group are smaller than the spaces between adjacent fingers belonging to different groups.

27. A method for making a gel-forming insert for use in defining one or more sample-receiving wells in an electrophoresis gel when a gel is polymerized around the insert, wherein the insert comprises a substantially rectangular planar body member having two long edges and two short edges, and upper and lower faces, and said body member comprises a base portion extending along a first of the long edges and an insert portion extending along a second of the long edges, wherein the base portion is formed from a rigid material and the insert portion is formed from an inherently flexible and compliant material, different from the rigid material, wherein the insert portion is in the form of a continuous solid blade effective to form a single sample receiving through or is divided into a plurality of fingers, each pair of fingers having substantially parallel edges which define a gap lying between the fingers in which gel will polymerize when the insert is used to form an electrophoresis gel; and wherein the edge of the insert portion is beveled at an angle of from 30 to 60 degrees such that the lower surface of the body member is larger than the upper surface, said method comprising the steps of:

(a) providing a mold for defining the shape of the insert portion;

(b) inserting the base portion into the mold;

(c) filling the mold with the flexible material, wherein the flexible material forms the insert portion and at least partially coats the base portion to adhere the insert portion to the base portion; and (d) removing the gel-forming insert from the mold.

28. The method of claim 27, wherein the flexible material is silicone.

29. The method of claim 28, wherein the rigid material is metal.

30. The method of claim 27, wherein mold is shaped such that the insert portion is divided into a plurality of fingers to define a plurality of sample-receiving wells, and each finger is separated from adjacent fingers by a space into which gel can flow to provide a barrier between adjacent sample-receiving wells.

31. The method of claim 30, wherein each finger is wider than the space between adjacent fingers.

32. The method of claim 30, wherein the fingers are formed in groups of four, and the spaces between fingers within a group are smaller than the spaces between adjacent fingers belonging to different groups.

* * * * *